United States Patent [19]

Lambert et al.

[11] Patent Number: 4,623,632

[45] Date of Patent: Nov. 18, 1986

[54] CATALYTIC COMPOSITE FOR CONVERSION OF HYDROCARBONS AND THE METHOD OF PREPARATION AND USE THEREOF

[75] Inventors: Susan L. Lambert, Rolling Meadows; Russell W. Johnson, Villa Park; Randy J. Lawson, Arlington Heights; Tery L. Barr, Northbrook, all of Ill.

[73] Assignee: Uop Inc., Des Plaines, Ill.

[21] Appl. No.: 668,102

[22] Filed: Nov. 5, 1984

[51] Int. Cl.$^4$ ............................................. B01J 29/04
[52] U.S. Cl. ......................................... 502/74; 502/66
[58] Field of Search ................................... 502/66, 74

[56] References Cited

U.S. PATENT DOCUMENTS 4,478,706 10/1984 Cohen .................................. 208/138

FOREIGN PATENT DOCUMENTS 3222143 12/1983 Fed. Rep. of Germany ........ 502/74

Primary Examiner—Carl F. Dees
Attorney, Agent, or Firm—Thomas K. McBride; John F. Spears, Jr.

[57] ABSTRACT

A novel catalytic composite, method of preparation, and process for the conversion of hydrocarbons is disclosed. The novel catalyst comprises a nonacidic zeolite having deposited thereon catalytically effective amounts of a Group VIII metal component and sufficient surface-deposited alkali metal to provide a surface-deposited alkali metal index of at least 10.

12 Claims, 1 Drawing Figure

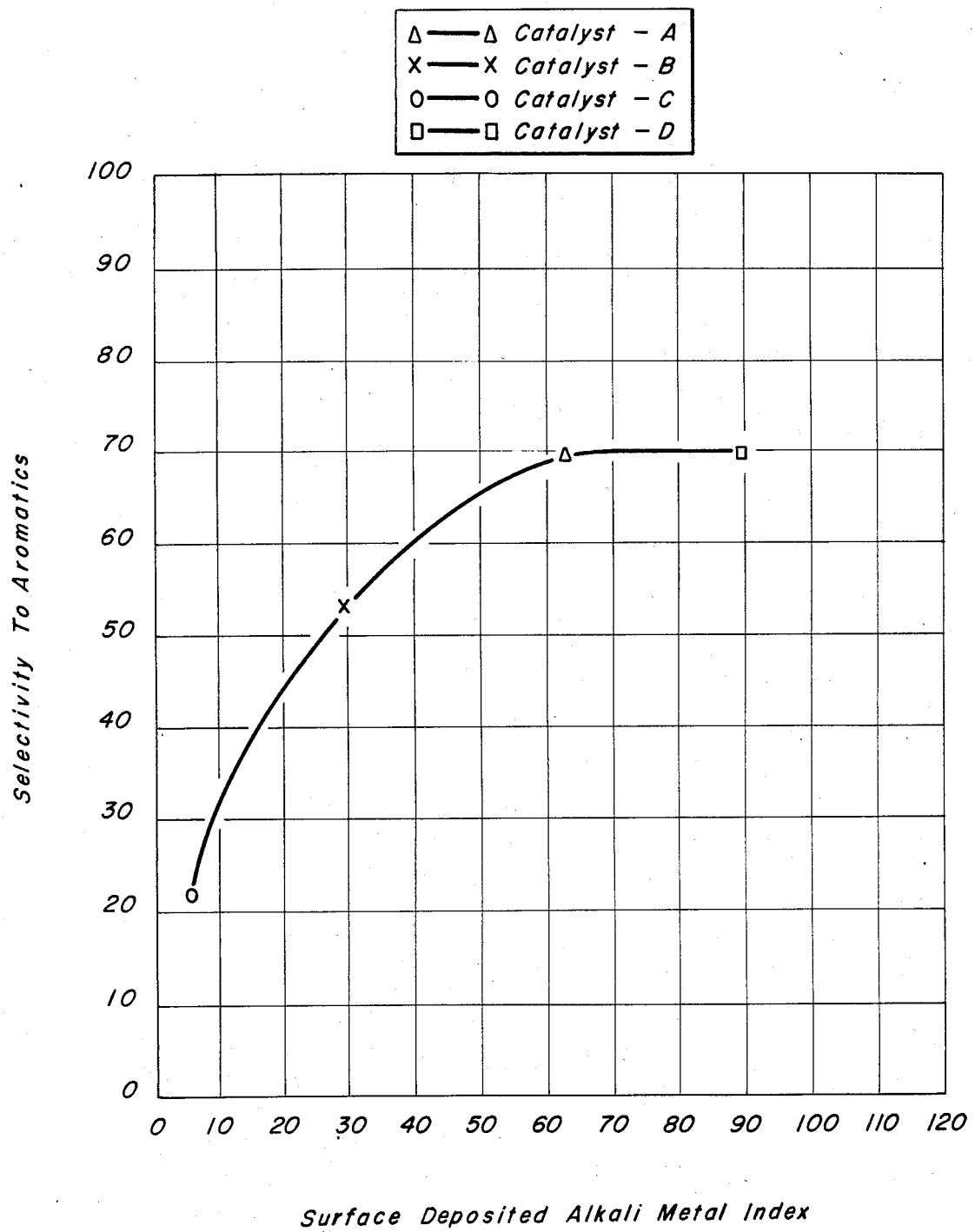

CATALYTIC COMPOSITE FOR CONVERSION OF HYDROCARBONS AND THE METHOD OF PREPARATION AND USE THEREOF

BACKGROUND OF THE INVENTION

The present invention is directed toward a novel catalytic composite for the conversion of hydrocarbons and especially for effecting the dehydrocyclization of aliphatic hydrocarbons to aromatics. More particularly, the novel catalytic composite enables the conversion of $C_6$-plus paraffins to their corresponding aromatics with a high degree of selectivity thereby enabling the facile production of large quantities of aromatics.

In the past it has become the practice to effect conversion of aliphatic hydrocarbons to aromatics by means of the well-known catalytic reforming process. In catalytic reforming a hydrocarbonaceous feedstock, typically a petroleum naphtha fraction, is contacted with a Group VIII-containing catalytic composite to produce a product reformate of increased aromatics content. The naphtha fraction is typically a full boiling range fraction having an initial boiling point of from 50° to about 100° F. and an end boiling point of from about 325° to about 425° F. Such a full boiling range naphtha contains significant amounts of $C_6$-plus paraffinic hydrocarbons and $C_6$-plus naphthenic hydrocarbons. As is well known these paraffinic and naphthenic hydrocarbons are converted to aromatics by means of multifarious reaction mechanisms. These mechanisms include dehydrogenation, dehydrocyclization, isomerization followed by dehydrogenation. Accordingly, naphthenic hydrocarbons are converted to aromatics by dehydrogenation. Paraffinic hydrocarbons may be converted to the desired aromatics by dehydrocyclization and may also undergo isomerization. Accordingly then, it is apparent that the number of reactions taking place in a catalytic reforming zone are numerous and the typical reforming catalyst must be capable of effecting numerous actions to be considered usable in a commercially feasible reaction system.

Because of the complexity and number of reaction mechanisms ongoing in catalytic reforming, it has become a recent practice to develop highly specific catalysts tailored to convert only specific reaction species to aromatics. Such catalysts would offer advantages over the typical reforming catalyst which must be capable of taking part in numerous reaction mechanisms. Accordingly, ongoing work has been directed toward producing a catalyst for the conversion of paraffinic hydrocarbons, particularly having six carbon atoms or more, to the corresponding aromatic hydrocarbon. Such a catalyst can be expected to be much more specific resulting in less undesirable side reactions such as hydrocracking. As can be appreciated by those of ordinary skill in the art, increased production of aromatics is desirable. The increased aromatic content of gasolines, a result of lead phase down, as well as demands in the petrochemical industry make $C_6$-$C_8$ aromatics highly desirable products. It is, therefore, very advantageous to have a catalytic composition which is highly selective for the conversion of less valuable $C_6$-plus paraffins to the more valuable $C_6$-plus aromatics.

OBJECTS AND EMBODIMENTS

It is, therefore, a principal object of our invention to provide a catalytic composite, and a method of making and using the same for the conversion of hydrocarbons. A corollary objective is to provide a process for the conversion of $C_6$-plus paraffinic hydrocarbons, especially $C_6$-$C_8$ paraffinic hydrocarbons, to their corresponding aromatics.

Accordingly, a broad embodiment of the present invention is directed toward a catalytic composite comprising a nonacidic zeolite having deposited thereon catalytically effective amounts of a Group VIII metal component and sufficient surface-deposited alkali metal to provide a surface-deposited alkali metal index of at least 10.

An alternative broad embodiment of the present invention is a hydrocarbon conversion process characterized in that it comprises contacting at hydrocarbon conversion conditions, a hydrocarbon charge stock with a catalytic composite comprising a nonacidic zeolite having deposited thereon catalytically effective amounts of a Group VIII metal component and sufficient surface-deposited alkali metal to provide a surface-deposited alkali metal index of at least 10.

A further embodiment of the present invention comprises a method of preparing a catalytic composite comprising contacting a nonacidic zeolite with catalytically effective amounts of a Group VIII metal component and with sufficient alkali metal to provide a surface-deposited alkali metal index of at least 10.

These as well as other objects and embodiments will become evident from the following, more detailed description of the present invention.

INFORMATION DISCLOSURE

Alumino-silicates containing alkali metals are well known in the art. For example, U.S. Pat. No. 3,013,986, issued Dec. 19, 1968, discloses an alkali metal loaded L-zeolite. In particular this reference indicates that the potassium or the potassium/sodium form of the L-zeolite are the preferred starting materials for the alkali metal-loaded L-zeolite. The reference teaches that a dehydrated molecular sieve may be contacted with alkali metal vapors to produce an alkali metal-loaded molecular sieve wherein the alkali metal is contained within the interior of the zeolitic molecular sieve. The reference, however, does not disclose a nonacidic zeolite having composited therewith catalytically effective amounts of Group VIII metal component and surface-deposited alkali metal. Moreover, the reference does not disclose that such a composition would have any use as a hydrocarbon conversion catalyst.

U.S. Pat. No. 3,376,215, issued Apr. 2, 1968, discloses a hydrocarbon conversion catalyst comprising a cocatalytic solid support containing a Group VIII metal which support comprises (1) an adsorbent refractory inorganic oxide and (2) a mordenite structure zeolite having deposited thereon about 10 to about 1000 ppm by weight, based on zeolite, of a metal selected from the class of alkali metals, alkaline earth metals and mixtures thereof. This reference teaches that the support comprising a mordenite form zeolite and a refractory oxide be cocatalytic. By way of contrast, an essential feature of the present invention is use of a nonacidic zeolite. In its nonacidic form the zeolite of the present invention cannot be considered catalytic. Rather the nonacidic zeolite acts to modify the catalytic Group VIII metal of the present invention. Accordingly, this reference does not disclose the novel catalyst of the present invention.

U.S. Pat. No. 3,755,486, issued Aug. 28, 1973, discloses a process for dehydrocyclizing $C_6$-$C_{10}$ hydrocarbons having at least a $C_6$ backbone using an Li, Na, or K zeolite X or Y or faujasite impregnated with 0.3 to 1.4% platinum. This reference, however, fails to disclose the advantages to be derived by utilizing a catalytic composite comprising a nonacidic zeolite having surface-deposited alkali metal. Likewise U.S. Pat. No. 3,819,507, issued June 25, 1974, and U.S. Pat. No. 3,832,414, issued Aug. 27, 1974, while disclosing processes similar to that of U.S. Pat. No. 3,755,486 both fail to teach the use and advantages to be derived by such use of a nonacidic zeolite composited with platinum and surface-deposited alkali metal.

U.S. Pat. No. 4,140,320, issued Aug. 1, 1978, discloses a process for dehydrocyclizing aliphatic hydrocarbons utilizing a type L-zeolite having exchangeable cations of which at least 90% are alkali metal ions selected from the group consisting of ions of sodium, lithium, potassium, rubidium and cesium and containing at least one metal selected from the group which consists of metals of Group VIII, tin and germanium. This reference fails to disclose the catalytic composite of the present invention in that the alkali metal ions of the catalyst of this reference are all associated with ion exchange sites on the L-zeolite. There is no disclosure of an L-zeolite having surface-deposited alkali metal. U.S. Pat. No. 4,417,083, issued Nov. 22, 1983, discloses a process for dehydrocyclization utilizing a substantially nonacidic zeolite having a pore diameter larger than 6.5 Å and containing at least one metal selected from the group consisting of platinum, rhenium, iridium, tin and germanium. Additionally, the catalyst contains sulfur and alkaline cations. However, in this reference there is no disclosure of surface-deposited alkali metal.

U.S. Pat. No. 4,416,806, issued Nov. 22, 1983, discloses yet another paraffin dehydrocyclization catalyst comprising platinum, rhenium as a carbonyl, and sulfur on a zeolitic crystalline alumino-silicate compensated in more than 90% by alkaline cations and having a pore diameter of more than 6.5 Angstroms. This reference too, fails to disclose a catalytic composition for dehydrocyclization having surface-deposited alkali metal.

Recent U.S. Pat. No. 4,430,200, issued Feb. 7, 1984, discloses a hydrocarbon conversion catalyst comprising a high silica zeolite such as mordenite or zeolite Y which has been base exchanged with an alkali metal. This reference too, however, fails to disclose a catalyst with surface-deposited alkali metal. Moreover, the reference merely discloses the use of the prior art catalyst in a cracking process and not a dehydrocyclization process.

Recent U.S. Pat. No. 4,448,891, issued May 15, 1984, discloses a dehydrocyclization catalyst comprising an L-zeolite which has been soaked in an alkali solution having a pH of at least 11 for a time and at a temperature effective to increase the period of time over which the catalytic activity of the catalyst is maintained. Additionally, the catalyst contains a Group VIII metal. However, in the reference the alkali soak is taught as modifying the silica content of the L-zeolite and altering the structure thereof. After the alkali soak the reference indicates that the L-zeolite is washed to remove excess ions. Accordingly, the catalyst of this reference does not have deposited thereon surface-deposited alkali metal. It, therefore, does not disclose the catalyst of the instant invention.

In summary then, the art has not recognized a catalytic composite for the conversion of hydrocarbons, especially the dehydrocyclization of $C_6$-plus paraffins to aromatics, comprising a nonacidic zeolite having deposited thereon catalytically effective amounts of a Group VIII metal component and sufficient surface-deposited alkali metal to result in a surface-deposited alkali metal index of at least 10. Moreover, the art has not recognized the attendant advantages to be derived from such a novel catalyst and use thereof.

DETAILED DESCRIPTION OF THE INVENTION

To reiterate briefly the present invention relates to a catalytic composite comprising a nonacidic zeolite having deposited thereon catalytically effective amounts of a Group VIII metal component and sufficient surface-deposited alkali metal to provide a surface-deposited alkali metal index of at least 10. Moreover, the catalytic composition of the invention has particular utility as a catalyst for the dehydrocyclization of $C_6$-plus paraffins, especially $C_6$–$C_{10}$ paraffins.

As heretofore indicated it is an essential feature of the catalyst of the present invention that it comprise a nonacidic zeolite. By "nonacidic zeolite" it is to be understood that it is meant that the zeolite has substantially all of its cationic sites of exchange occupied by nonhydrogen cationic species. Preferably such cationic species will comprise the alkali metal cations although other cationic species may be present. Irrespective of the actual cationic species present in the sites of exchange, the nonacidic zeolite in the present invention has substantially all of the cationic sites occupied by nonhydrogen cations thereby rendering the zeolite substantially fully cationic exchanged. Many means are well known in the art for arriving at a substantially fully cationic exchanged zeolite and thus they need not be elaborated herein. The nonacidic zeolite of the present invention acts to modify the catalytic Group VIII metal and is substantially inert in the reaction. Hence, the nonacidic zeolite support of the present invention is noncatalytic and an essential feature of the present invention is that it be such.

Typical of the nonacidic zeolites which may be utilized in the present invention are X-zeolite, Y-zeolite and mordenite. Especially preferred in application of the present invention is L-zeolite. Of course, all of these zeolites must be in nonacidic form as defined above and, therefore, the cationic exchangeable sites are substantially fully cationic exchanged with nonhydrogen cationic species. As also indicated above, typically the cations occupying the cationic exchangeable sites will comprise one or more of the alkali metals including lithium, sodium, potassium, rubidium and cesium. Accordingly then, the nonacidic zeolite of the present invention may comprise the sodium forms of X-zeolite, Y-zeolite or mordenite. An especially preferred nonacidic zeolite for application in the present invention is the potassium form of L-zeolite. It should also be understood, however, that the nonacidic zeolite of the invention may contain more than one type of the alkali metal cation at the cationic exchangeable sites, for example, sodium and potassium. As will be explained more fully hereinafter this can occur as the result of competitive cationic exchanges which may take place during the deposition of the surface-deposited alkali metal.

Irrespective of the particular nonacidic zeolite utilized the catalyst of the present invention also comprises catalytically effective amounts of a Group VIII metal component, including catalytically effective amounts of nickel component, rhodium component, palladium component, iridium component, platinum component or mixtures thereof. Especially preferred among the Group VIII metal components is a platinum component. The Group VIII metal component may be deposited on the nonacidic zeolite by any suitable means known in the art. For example, a platinum component may be impregnated into the nonacidic zeolite from an appropriate solution such as a dilute chloroplatinic acid solution. Alternatively, the Group VIII metal component may be deposited on the nonacidic zeolite by means of ion exchange in which case some of the cationic exchange sites of the nonacidic zeolite will contain Group VIII metal cations. After ion exchange the Group VIII metal may be subject to a low temperature oxidation prior to any reduction step. The Group VIII metal component may be deposited on the nonacidic zeolite either prior or subsequent to the deposition of the hereinafter described surface-deposited alkali metal.

Irrespective of the exact method of depositing the Group VIII metal component, any catalytically effective amount of Group VIII metal component may be employed. The optimum Group VIII metal component content will depend generally on which Group VIII metal component is utilized in the catalyst of the invention. However, generally from about 0.01 to about 5.0 wt. % of the Group VIII metal component based on the weight of the zeolite, Group VIII metal component and surface-deposited alkali metal may be advantageously deposited on the zeolite.

It should further be understood that best results are achieved when the Group VIII metal component is highly dispersed on the nonacidic zeolite. The Group VIII metal component is most effective in a reduced state. Any suitable means may be employed for reducing the Group VIII metal component and many are well known in the art. For example, after deposition on the nonacidic zeolite the Group VIII metal component may be subjected to contact with a suitable reducing agent, such as hydrogen, at an elevated temperature for a period of time.

In addition to comprising a Group VIII metal component it is contemplated in the present invention, that the catalyst thereof may contain other metal components well known to have catalyst modifying properties. Such metal components include components of rhenium, tin, cobalt, indium, gallium, lead, zinc, uranium, thallium, dysprosium, and germanium, etc. Incorporation of such metal components have proven beneficial in catalytic reforming as promoters and/or extenders. Accordingly, it is within the scope of the present invention that catalytically effective amounts of such modifiers may be beneficially incorporated into the catalyst of the present invention improving its performance.

Irrespective of the particular Group VIII metal component and catalytic modifiers composited with the nonacidic zeolite, the catalyst of the present invention also comprises sufficient surface-deposited alkali metal to provide a surface-deposited alkali metal index of at least 10 and preferably from about 40 to about 500. It is to be understood that by surface-deposited alkali metal it is meant that the alkali metal component is not associated with a cationic exchangeable site, but rather is excess alkali metal component above that amount required to occupy substantially all of the cationic exchangeable sites. It is to be further understood that the surface-deposited alkali metal index is indicative of the amount of such surface-deposited alkali metal. As used herein the term "surface-deposited alkali metal index" is defined as $10^4$ multiplied by the moles per liter of soluble alkali metal yielded by 0.5 g of catalytic composition placed in 10 cc of deionized water as measured by an electrode sensitive to said alkali metal at 25° C.

Any of the alkali metals may be used as the surface-deposited alkali-metal including lithium, sodium, potassium, rubidium, cesium and mixtures thereof. The surface-deposited alkali metal giving the best results will depend on the particular nonacidic zeolite used. Potassium on the potassium form of L-zeolite is especially preferred. Additionally, sodium on the sodium form of X-zeolite or Y-zeolite may also be advantageously employed.

It should be understood that the surface-deposited alkali metal need not necessarily be the same alkali metal as the cations occupying the cationic exchangeable sites of the nonacidic zeolite. Hence, the surface-deposited alkali metal may, for example, comprise potassium while the nonacidic zeolite may comprise the sodium form of X-zeolite or Y-zeolite. Likewise, the surface-deposited alkali metal may comprise more than one alkali metal. Accordingly, the surface-deposited alkali metal may, for example, comprise potassium and sodium on the sodium form of X-zeolite or Y-zeolite.

The surface-deposited alkali metal may be composited with the nonacidic zeolite by any suitable technique. For example, standard impregnation techniques may be employed utilizing an aqueous solution of an alkali metal salt. It is preferred that basic alkali metal salts be utilized over neutral salts. For example, when surface-depositing potassium on the potassium form of L-zeolite it is preferred that the impregnation solution comprise a basic salt of potassium such as $KHCO_3$, $K_2CO_3$, $KOH$, etc. rather than comprising a neutral potassium salt such as KCl.

It should further be noted that when it is desired to have a surface-deposited alkali metal different than the alkali metal cation associated with the cation exchangeable sites of the nonacidic zeolite, some amount of competitive ion exchange may take place during impregnation. For example, when surface depositing potassium on the sodium form of Y-zeolite, a competitive ionic exchange may take place wherein some of the potassium from the impregnation solution replaces some of the sodium on the cationic exchangeable sites of the nonacidic Y-zeolite. In turn this displaced sodium will be surface-deposited on the zeolite along with the balance of the potassium. The net result is that the cations at the cationic exchangeable sites will comprise sodium and potassium ions while the surface-deposited alkali metal will comprise sodium and potassium. A catalyst having such a distribution is within the scope of the present invention, but may not give the best results. There are, however, techniques known in the art of catalyst preparation to minimize the problem of competitive exchange and further elaboration of such techniques for one of ordinary skill in the art is unnecessary.

It is to be further understood that the catalytic composition of the present invention may be utilized in bound or unbound form. As is well known in the art the use of a binder enhances the physical strength of the catalyst. Additionally, binding the catalyst allows formation of shapes suitable for use in catalytic conversion processes. For example, by use of a binder the catalyst of the instant invention may be formulated into spheres. The use of spheres is well known to be advantageous in various applications. In particular when the catalyst of the instant invention is emplaced within a continuously moving bed system a spherical shape enhances the ability of the catalyst to move easily through the reaction zones. Of course, other shapes may be employed where advantageous. Accordingly, the catalyst of the instant invention may be formed into the shape of an extrudate, saddle, etc.

Regardless of the exact shape selected from the catalytic composite of the present invention, any binder typically utilized to bind zeolitic-based compositions may be employed. Such binders are well known in the art and include clays, bauxite, refractory inorganic oxides such as alumina, zirconium dioxide, hafnium oxide, beryllium oxide, vanadium oxide, cesium oxide, chromium oxide, zinc oxide, magnesia, thoria, boria, silica-magnesia, chromia-alumina, alumina-boria, etc. A particularly preferred binder is silica. It is further preferred that the binder be substantially inert to the catalytic composition of the present invention and to the reactants to be converted by the catalysts. The catalytic composition of the present invention may be bound by any method known in the art. Such methods include pilling, extruding, oil-dropping, granulating, marumarizing, etc.

Irrespective of its exact shape and size, the catalytic composition of the present invention has particular utility as a hydrocarbon conversion catalyst. Accordingly, a hydrocarbon charge stock is contacted at hydrocarbon conversion conditions with the catalytic composite of the present invention. A wide range of hydrocarbon conversion conditions may be employed and will depend upon the particular charge stock and reaction to be effected. Generally, these conditions include a temperature of about 32° to about 1500° F., a pressure of from atmospheric to about 100 atmospheres, a liquid hourly space velocity (calculated on the basis of equivalent liquid volume of the charge stock contacted with the catalyst per hour divided by the volume of conversion zone containing catalyst) of about 0.2 hr.$^{-1}$ to 15 hr.$^{-1}$. Furthermore, hydrocarbon conversion conditions may include the presence of a diluent such as hydrogen. When such is the case the hydrogen to hydrocarbon mole ratio may be from about 0.5:1 to about 30:1.

A particularly preferred application of the catalyst of the present invention is its use as a dehydrocyclization catalyst and in particular for the dehydrocyclization of $C_6$-$C_8$ nonaromatic hydrocarbons. Accordingly, a hydrocarbon charge stock comprising $C_6$-$C_8$ nonaromatic hydrocarbons is contacted with the catalyst of the present invention at dehydrocyclization conditions. Dehydrocyclization conditions include a pressure of from about 0 psig to about 1000 psig, with the preferred pressure being from about 50 psig to about 600 psig, a temperature of from about 800° to about 1200° F., and a liquid hourly space velocity of from about 0.1 hr.$^{-1}$ to about 10 hr.$^{-1}$. Preferably, hydrogen may be employed as a diluent. When present, hydrogen may be circulated at a rate of from about 1 to about 10 moles of hydrogen per mole of hydrocarbon.

According to the present invention a hydrocarbon charge stock is contacted with the catalyst of the present invention in a hydrocarbon conversion zone. This contacting may be accomplished by using the catalyst in a fixed-bed system, a moving-bed system, a fluidized-bed system, or in a batch-type operation. The hydrocarbon charge stock and, if desired, a hydrogen-rich gas as diluent are typically preheated by any suitable heating means to the desired reaction temperature and then are passed into a conversion zone containing the catalyst of the invention. It is, of course, understood that the conversion zone may be one or more separate reactors with suitable means therebetween to ensure that the desired conversion temperature is maintained at the entrance to each reactor. It is also important to know that the reactants may be contacted with the catalyst bed in either upward, downward, or radial-flow fashion with the latter being preferred. In addition the reactants may be in the liquid phase, a mixed liquid-vapor phase, or a vapor phase when they contact the catalyst. Best results are obtained when the reactants are in the vapor phase.

In the case where the catalyst of the present invention is employed in a dehydrocyclization process, the dehydrocyclization system will comprise a reaction zone containing the catalyst of the present invention. As indicated heretofore the catalyst may be utilized within the reaction zone as a fixed-bed system, a moving-bed system, a fluidized-bed system, or in a batch-type operation; however, in view of the operational advantages well recognized in the art it is preferred to utilize the catalyst of the present invention in a moving-bed system. In such a system the reaction zone may be one or more separate reactors with heating means therebetween to compensate for the endothermic nature of the dehydrocyclization reaction that takes place in each catalyst bed. The hydrocarbon feedstream, preferably comprising $C_6$-$C_8$ nonaromatic hydrocarbons, is charged to the reaction zone as a continuous moving bed. Therein it is contacted with the hydrocarbon charge stock to effect the dehydrocyclization thereof.

After contact with the catalyst of the present invention the hydrocarbon charge stock having undergone dehydrocyclization is withdrawn as an effluent stream from the reaction zone and passed through a cooling means to a separation zone. In the separation zone the effluent may be separated into various constituents depending upon the desired products. When hydrogen is utilized as a diluent in the reaction zone the separation zone will typically comprise a vapor-liquid equilibrium separation zone and a fractionation zone. A hydrogen-rich gas is separated from a high octane liquid product containing aromatics generated within the dehydrocyclization zone. After separation at least a portion of the hydrogen-rich gas may be recycled back to the reaction zone as diluent. The balance of the hydrogen-rich gas may be recovered for use elsewhere. The high octane liquid product comprising aromatics may then be passed to a fractionation zone to separate aromatics from the unconverted constituents of the charge stock. These unconverted constituents may then be passed back to the reaction zone for processing or to other processes for utilization elsewhere.

A wide range of hydrocarbon charge stocks may be employed in the process of the present invention. The exact charge stock utilized will, of course, depend on the precise use of the catalyst. Typically, hydrocarbon charge stocks which may be used in the present invention will contain naphthenes and paraffins, although in some cases aromatics and olefins may be present. Accordingly, the class of charge stocks which may be utilized includes straight-run naphthas, natural naphthas, synthetic naphthas, and the like. Alternatively straight-run and cracked naphthas may also be used to advantage. The naphtha charge stock may be a full-boiling range naphtha having an initial boiling point of from about 50° to about 150° F. and an end boiling point within the range of from about 325° to 425° F., or may be a selected fraction thereof which generally will be a higher boiling fraction commonly referred to as a heavy naphtha, for example, a naphtha boiling in the range of $C_7$-400° F. It is preferred that the charge stocks employed in the present invention be treated by conventional catalytic pretreatment methods such as hydrorefining, hydrotreating, hydrodesulfurization, etc., to remove substantially all sulfurous, nitrogenous and water-yielding contaminants therefrom.

When the catalyst of the present invention is utilized as a dehydrocyclization catalyst it is preferred that the charge stock substantially comprise paraffins. This, of course, is a result of the fact that the purpose of a dehydrocyclization process is to convert paraffins to aromatics. Because of the value of $C_6$–$C_8$ aromatics it is additionally preferred that the hydrocarbon charge stock comprise $C_6$–$C_8$ paraffins. However, notwithstanding this preference the hydrocarbon charge stock may comprise naphthenes, aromatics, and olefins in addition to $C_6$–$C_8$ paraffins.

In order to more fully demonstrate the attendant advantages arising from the present invention the following examples are set forth. It is to be understood that the following is by way of example only and is not intended as an undue limitation on the otherwise broad scope of the present invention.

It should be understood that there are three parameters useful in evaluating hydrocarbon conversion catalyst performance, and in particular in evaluating and comparing dehydrocyclization catalysts. The first is "activity" which is a measure of the catalyst's ability to convert reactants at a specified set of reaction conditions. The second catalyst performance criteria is "selectivity" which is an indication of the catalyst's ability to produce a high yield of the desired product. The third parameter is "stability" which is a measure of the catalyst's ability to maintain its activity and selectivity over time. In the appended examples the criteria which will be of interest is catalyst selectivity. For purposes of the following, the catalyst of the invention is exemplified as a dehydrocyclization catalyst and the measure of catalyst selectivity is the conversion of the paraffin reactants to aromatics.

EXAMPLE I

A first catalyst was made in accordance with the invention. Fifty grams of potassium form L-zeolite having an average crystallite size of 275 Å were slurried in a solution of 12.8 grams of potassium bicarbonate and 100 cc of deionized water. The potassium/zeolite slurry was evaporated to dryness and then calcined in air at 480° C. for 3 hours. The resulting potassium-impregnated zeolite was then subjected to an ion exchange step in order to composite platinum thereon. This was effected by placing the potassium-impregnated zeolite into 200 cc of a 0.020M. $Pt(NH_3)_4Cl_2$/0.90M. KCl solution. After 3 days at 25° C., the potassium-impregnated, platinum-containing zeolite was filtered from the ion exchange solution and rinsed with 1200 cc of deionized $H_2O$. The resulting catalyst was then calcined and reduced at 350° C. The resulting catalyst contained about 0.7 wt. % of platinum and had a surface deposited alkali metal index of about 61. This first catalyst made in accordance with the invention was designated Catalyst "A."

EXAMPLE II

A second catalyst was prepared by the following method. Fifty grams of potassium form L-zeolite already containing surface deposited alkali metal was subjected to an ion-exchange step to deposit platinum thereon. The ion exchange step was effected substantially as before utilizing an ion exchange solution comprising $Pt(NH_3)_4Cl_2$ with KCl. The ion exchanged platinum- and surface-deposited potassium-containing L-zeolite was then rinsed, calcined and reduced as before. The finished catalyst contained about 0.7 wt. % platinum and had a surface deposited alkali metal index of about 28. This catalyst was designated Catalyst "B."

EXAMPLE III

A third catalyst was prepared in this example. A potassium form of L-zeolite was subjected to ion-exchange with a platinum and KCl containing ion exchange solution. Before ion exchange the platinum-containing L-zeolite was subjected to substantial washing in deionized water to assure removal of surface-deposited potassium which might be on the zeolite. The L-zeolite was then calcined and reduced as before. The finished catalyst contained about 1.3 wt. % platinum and had a surface-deposited alkali metal index of about 7. This catalyst was designated as Catalyst "C."

EXAMPLE IV

A fourth catalyst was prepared by slurrying 50 grams of potassium form L-zeolite with an aqueous solution of $K_2CO_3$. The potassium/zeolite solution was evaporated to dryness and was subjected to calcination as before. Thereafter the potassium impregnated zeolite was subjected to an ion exchange step for the deposition of platinum. The ion-exchange solution comprised a solution of $Pt(NH_3)_4Cl_2$/KCl. The resulting composite was thereafter rinsed, calcined and reduced as in the above examples. The resulting catalyst contained about 0.6 wt. % platinum and had a surface-deposited alkali metal index of about 89. This catalyst was designated Catalyst "D."

EXAMPLE V

The above four Catalysts A, B, C and D were all subjected to a test to measure their respective performance as dehydrocyclization catalysts. The results of this test are set forth in FIG. 1. FIG. 1 is a plot of catalyst selectivity for the production of aromatics as a function of the surface-deposited alkali metal index.

The charge stock utilized in this example had the following analysis:

| | |
|---|---:|
| $C_3$/$C_4$/$C_5$ paraffins | 0.4 wt. % |
| $C_6$ paraffins | 69.5 wt. % |
| $C_6$ naphthenes | 0.7 wt. % |
| $C_7$ paraffins | 21.4 wt. % |
| $C_7$ naphthenes | 8.0 wt. % |
| Total | 100.0 wt. % |

The test was run in a pilot plant having a reactor in which the catalyst to be tested was emplaced. The reactor effluent was analyzed by means of an on-line gas chromatograph.

The conditions employed during testing of the catalysts were a reaction zone inlet temperature of 500° C., a 1.0 hr.$^{-1}$ liquid hourly space velocity and a reaction zone pressure of 50 psig. Hydrogen was admixed with the charge stock prior to contact with the catalysts. Sufficient hydrogen on a once through basis was used to provide a 5:1 ratio of moles of hydrogen to moles of hydrocarbon charge stock. The procedure followed in testing was to first contact the catalyst with the charge stock at a reaction zone temperature of 410° C. The 410° C. reaction zone inlet temperature was maintained for a period of 7 hours. Thereafter the reaction zone inlet temperature was increased to 500° C. over a 3 hour period. The 500° C. temperature was then maintained over a 12 hour test period during which the reaction zone effluent was analyzed by the on-line gas chromatograph each hour.

Results from the tests are set forth in FIG. 1. For purposes of FIG. 1 and the following discussion, selectivity is defined as the grams of aromatics produced per gram of feed converted multiplied by 100. Surprisingly and unexpectedly, it can be seen from the data in FIG. 1 that as the surface deposited-alkali metal index increases beyond 10, there is an increase in the selectivity for the production of aromatics when the catalysts are employed in the dehydrocyclization process.

EXAMPLE VI

Two further Catalysts, E and F, were prepared substantially in accordance with the preparations heretofore set forth. Platinum was deposited by ion exchange on the L-zeolite utilizing a solution of $Pt(NH_3)_4Cl_2$; however, the ion exchange of Catalyst E was conducted at 25° C. while that of Catalyst F was 95° C. The platinum contents of Catalysts E and F were 1.38 and 1.55, respectively. Catalysts E and F also contained sufficient surface-deposited potassium to have surface-deposited alkali metal indexes of 129 and 45, respectively.

EXAMPLE VII

In order to determine their selectivities for the production of aromatics in dehydrocyclization, Catalysts E and F were subjected to substantially the same test set forth in Example V utilizing the same charge stock. However, in this example instead of using hydrogen on a once through basis, the hydrogen admixed with the charge stock was recycle hydrogen recovered from the reaction zone effluent. Additionally, in this test the reaction zone pressure was 100 psig and not 50 psig as in Example V.

Under the above-described test conditions both catalysts exhibited high selectivity for the production of aromatics from a highly paraffinic feed. Catalyst E had an aromatic selectivity of 70%. Catalyst F had an aromatic selectivity of 62%. Of special interest is the fact that both catalysts exhibit high selectivities for aromatic production.

We claim as our invention:

1. A catalytic composite comprising a nonacidic L-zeolite having deposited thereon catalytically effective amounts of a Group VIII metal component and sufficient surface-deposited alkali metal to provide a surface-deposited alkali metal index of at least 10.

2. The composite of claim 1 further characterized in that the Group VIII metal component comprises a platinum component.

3. The composite of claim 1 further characterized in that the surface-deposited alkali metal is selected from potassium, sodium or mixtures thereof.

4. The composite of claim 1 further characterized in that it comprises from about 0.01 to about 5.0 wt. % of the Group VIII metal component based on the weight of the zeolite, Group VIII metal component and surface-deposited alkali metal.

5. The composite of claim 1 further characterized in that there is sufficient surface-deposited alkali metal to provide a surface-deposited alkali metal index of from about 40 to about 500.

6. A catalytic composite comprising an L-zeolite having deposited thereon sufficient surface-deposited potassium to provide a surface-deposited alkali metal index of from about 40 to about 500 and from about 0.01 to about 5.0 wt. % of a platinum component based on the weight of the L-zeolite, the platinum component and the surface-deposited potassium.

7. A method of preparing a catalytic composite comprising contacting a nonacidic L-zeolite with catalytically effective amounts of a Group VIII metal component and with sufficient alkali metal to provide a surface-deposited alkali metal index of at least 10.

8. The method of claim 7 further characterized in that the Group VIII metal component comprises a platinum component.

9. The method of claim 7 further characterized in that the alkali metal is selected from potassium, sodium or mixtures thereof.

10. The method of claim 1 further characterized in that sufficient amounts of Group VIII metal component are used to result in a catalytic composite having from about 0.01 to about 5.0 wt. % of the Group VIII metal component based on the weight of the zeolite, Group VIII metal component and surface-deposited alkali metal.

11. The method of claim 1 further characterized in that sufficient amounts of alkali metal are used to provide a surface-deposited alkali metal index of from about 40 to about 500.

12. A method of preparing a catalytic composite comprising compositing L-zeolite with sufficient potassium to provide a surface-deposited alkali metal index of from about 40 to about 500 and from about 0.01 to about 5.0 wt. % of platinum component based on the weight of the L-zeolite, the platinum component and the surface-deposited potassium.

* * * * *